(12) United States Patent
Yoshida et al.

(10) Patent No.: US 10,271,933 B2
(45) Date of Patent: Apr. 30, 2019

(54) ELECTRIC TOOTHBRUSH DEVICE AND METHOD

(71) Applicants: COLGATE-PALMOLIVE COMPANY, New York, NY (US); OMRON HEALTHCARE CO., LTD, Terado-cho, Muko-shi, Kyoto (JP)

(72) Inventors: Hideaki Yoshida, Muko (JP); Mamoru Katano, Muko (JP)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/735,414

(22) PCT Filed: Jun. 9, 2016

(86) PCT No.: PCT/US2016/036611
§ 371 (c)(1),
(2) Date: Dec. 11, 2017

(87) PCT Pub. No.: WO2016/205055
PCT Pub. Date: Dec. 22, 2016

(65) Prior Publication Data
US 2018/0193122 A1    Jul. 12, 2018

(30) Foreign Application Priority Data

Jun. 18, 2015   (JP) .................................. 2015-122896
Jun. 19, 2015   (JP) .................................. 2015-124172

(51) Int. Cl.
*A61C 17/22*   (2006.01)
*A61C 17/34*   (2006.01)

(52) U.S. Cl.
CPC ............ *A61C 17/221* (2013.01); *A61C 17/34* (2013.01); *A61C 17/3418* (2013.01); *A61C 17/3481* (2013.01)

(58) Field of Classification Search
CPC ............ A46B 15/0002; A46B 15/0006; A46B 15/0008; A46B 15/0004; A06F 19/00; A61C 17/221
See application file for complete search history.

(56) References Cited

U.S. PATENT DOCUMENTS 9,882,986 B2 *   1/2018   Patel ...................... G16H 10/00
2009/0092955 A1 *   4/2009   Hwang ............... A46B 15/0002
434/263

(Continued)

FOREIGN PATENT DOCUMENTS

KR         2008 0053982         6/2008

OTHER PUBLICATIONS

International Search Report and the Written Opinion of the International Searching Authority issued in International Application PCT/US2016/036611 dated Oct. 26, 2016.

*Primary Examiner* — Shay Karls

(57) ABSTRACT

In one embodiment, the invention can be an electric toothbrush including a trajectory detecting module configured to detect a trajectory of movement of a brush, the trajectory including a plurality of positions; an attitude detecting module configured to detect an attitude of the brush; a site estimating module configured to estimate a brushing site for each of the plurality of positions of the trajectory, each estimated brushing site being based on the trajectory detected by the trajectory detecting module; and a back most tooth detecting module configured to detect a back most tooth based on a change of the attitude detected by the attitude detecting module; wherein the site estimating module is further configured to correct the estimated brushing site for each of the plurality of positions of the trajectory based on the estimated site of the detected back most tooth.

20 Claims, 15 Drawing Sheets

(56) References Cited

U.S. PATENT DOCUMENTS

2010/0145654 A1 6/2010 Hwang et al.
2011/0041269 A1 2/2011 Iwahori

* cited by examiner

ELECTRIC TOOTHBRUSH DEVICE AND METHOD

CROSS REFERENCE TO RELATED APPLICATIONS

The present application claims priority under 35 U.S.C. § 119 to Japanese Patent Application No. 2015-124172, filed Jun. 19, 2015, and Japanese Patent Application No. 2015-122896, filed Jun. 18, 2015, the disclosures of which are incorporated herein by reference.

BACKGROUND

Electric toothbrushes are popular devices for cleaning teeth. Some electric toothbrushes attempt to estimate the sites that the toothbrush has brushed. This information can be useful in correcting bad brushing habits and encouraging a more thorough brushing of all teeth. But such toothbrushes have difficulty providing accurate information. What is needed is an electric toothbrush device that can accurately estimate brushing sites.

BRIEF SUMMARY

The present disclosure is directed to an apparatus, method, and medium for estimating brushing sites. In one aspect, an electric toothbrush comprises a trajectory detecting module configured to detect a trajectory of movement of a brush, the trajectory comprising a plurality of positions; an attitude detecting module configured to detect an attitude of the brush; a site estimating module configured to estimate a brushing site for each of the plurality of positions of the trajectory, each estimated brushing site being based on the trajectory detected by the trajectory detecting module; and a back most tooth detecting module configured to detect a back most tooth based on a change of the attitude detected by the attitude detecting module; wherein the site estimating module is further configured to correct the estimated brushing site for each of the plurality of positions of the trajectory based on the estimated site of the detected back most tooth.

In another aspect, a method includes detecting a trajectory of movement of a brush, the trajectory comprising a plurality of positions; detecting an attitude of the brush; estimating a brushing site for each of the plurality of positions of the trajectory, each estimated brushing site being based on the trajectory detected; detecting a back most tooth based on a change of the attitude detected by the attitude detecting module; and correcting the estimated brushing site for each of the plurality of positions of the trajectory based on an estimated site of the detected back most tooth.

In another aspect, a non-transitory computer-readable storage medium encoded with instructions which, when executed on a processor, performs a method of detecting a trajectory of movement of a brush, the trajectory comprising a plurality of positions; detecting an attitude of the brush; estimating a brushing site for each of the plurality of positions of the trajectory, each estimated brushing site being based on the trajectory detected; and detecting a back most tooth based on a change of the attitude detected by the attitude detecting module; and correcting the estimated brushing site for each of the plurality of positions of the trajectory based on an estimated site of the detected back most tooth.

In yet another aspect, an electric toothbrush includes a driving module configured to oscillate a brush unit; an acceleration sensor configured to generate an output signal; a signal extraction module configured to extract from the output signal (a) a first signal having a frequency at a first threshold or higher and (b) a second signal having a frequency at a second threshold or lower; a brushing site estimation module configured to estimate a brushing site of the brush unit based on the output signal of the acceleration sensor; and a correction module configured to correct the brushing site estimated by the brushing site estimation module based on an amplitude of the first signal and an amplitude of the second signal.

In another aspect, a brushing site estimation method for an electric toothbrush includes extracting a first signal from an output signal of an acceleration sensor of an electric toothbrush, the first signal having a frequency at a first threshold or higher; extracting a second signal from the output signal of the acceleration sensor, the second signal having a frequency at a second threshold or lower; estimating a brushing site of the brush unit based on the output signal of the acceleration sensor; and correcting the brushing site estimated by the brushing site estimation module based on an amplitude of the first signal and an amplitude of the second signal.

In another aspect, a non-transitory computer-readable storage medium encoded with instructions which, when executed on a processor, perform a method of extracting a first signal from an output signal of an acceleration sensor of an electric toothbrush, the first signal having a frequency at a first threshold or higher; extracting a second signal from the output signal of the acceleration sensor, the second signal having a frequency at a second threshold or lower; estimating a brushing site of the brush unit based on the output signal of the acceleration sensor; and correcting the brushing site estimated by the brushing site estimation module based on an amplitude of the first signal and an amplitude of the second signal.

BRIEF DESCRIPTION OF THE DRAWINGS

The present disclosure will become more fully understood from the detailed description and the accompanying drawings, wherein.

DETAILED DESCRIPTION

Figure 1:
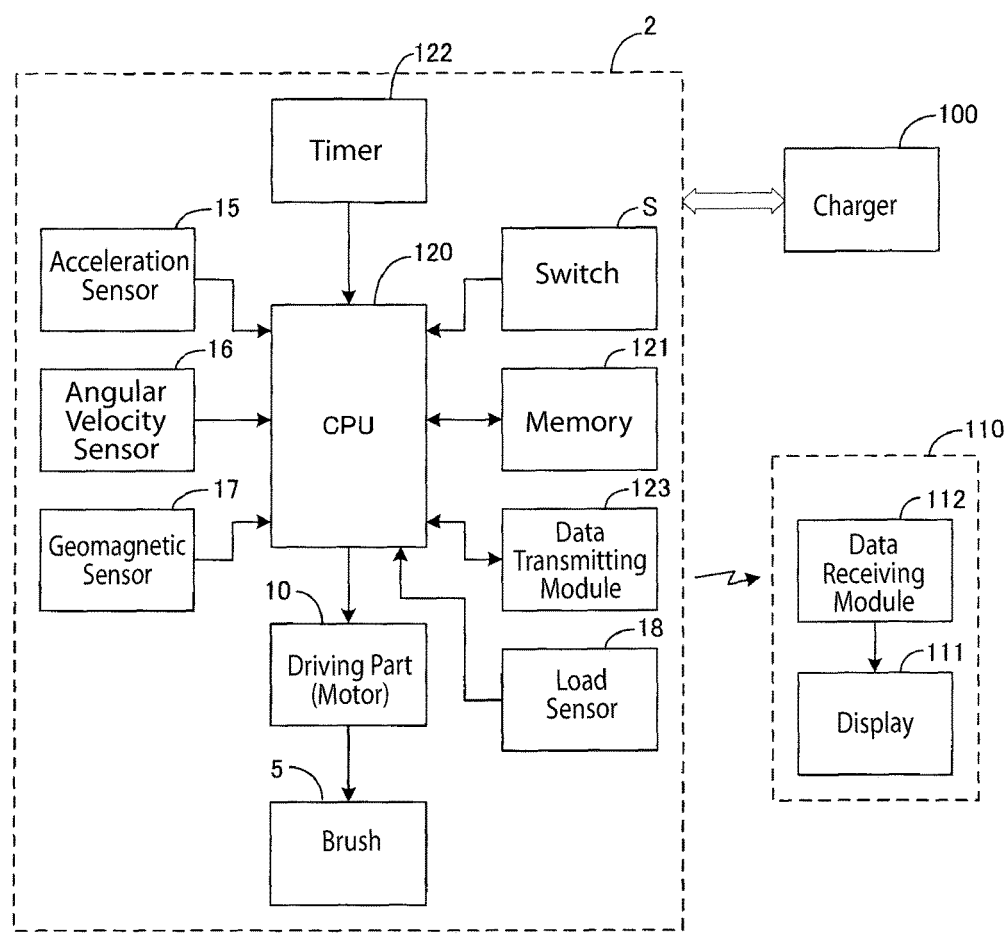
FIG. 1 is a block diagram illustrating an example configuration of an electric toothbrush for describing an embodiment.

The following description of the preferred embodiment(s) is merely exemplary in nature and is in no way intended to limit the invention or inventions. The description of illustrative embodiments is intended to be read in connection with the accompanying drawings, which are to be considered part of the entire written description. In the description of the exemplary embodiments disclosed herein, any reference to direction or orientation is merely intended for convenience of description and is not intended in any way to limit the scope of the present inventions. The discussion herein describes and illustrates some possible non-limiting combinations of features that may exist alone or in other combinations of features. Furthermore, as used herein, the term "or" is to be interpreted as a logical operator that results in true whenever one or more of its operands are true.

Features of the present inventions may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device", or "device", and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present inventions may be embodied in the form of computer-implemented processes and apparatuses such as processor-based data processing and communication systems or computer systems for practicing those processes. The present inventions may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

The disclosure is divided into two sections. Section I discusses a first electric toothbrush and method for estimating a brushing site. Section II discusses a second electric toothbrush and method for estimating a brushing site. To the extent a term, reference number, or symbol is used differently in different sections, context should be taken from the relevant section and not the other section.

Section I

Figure 2:
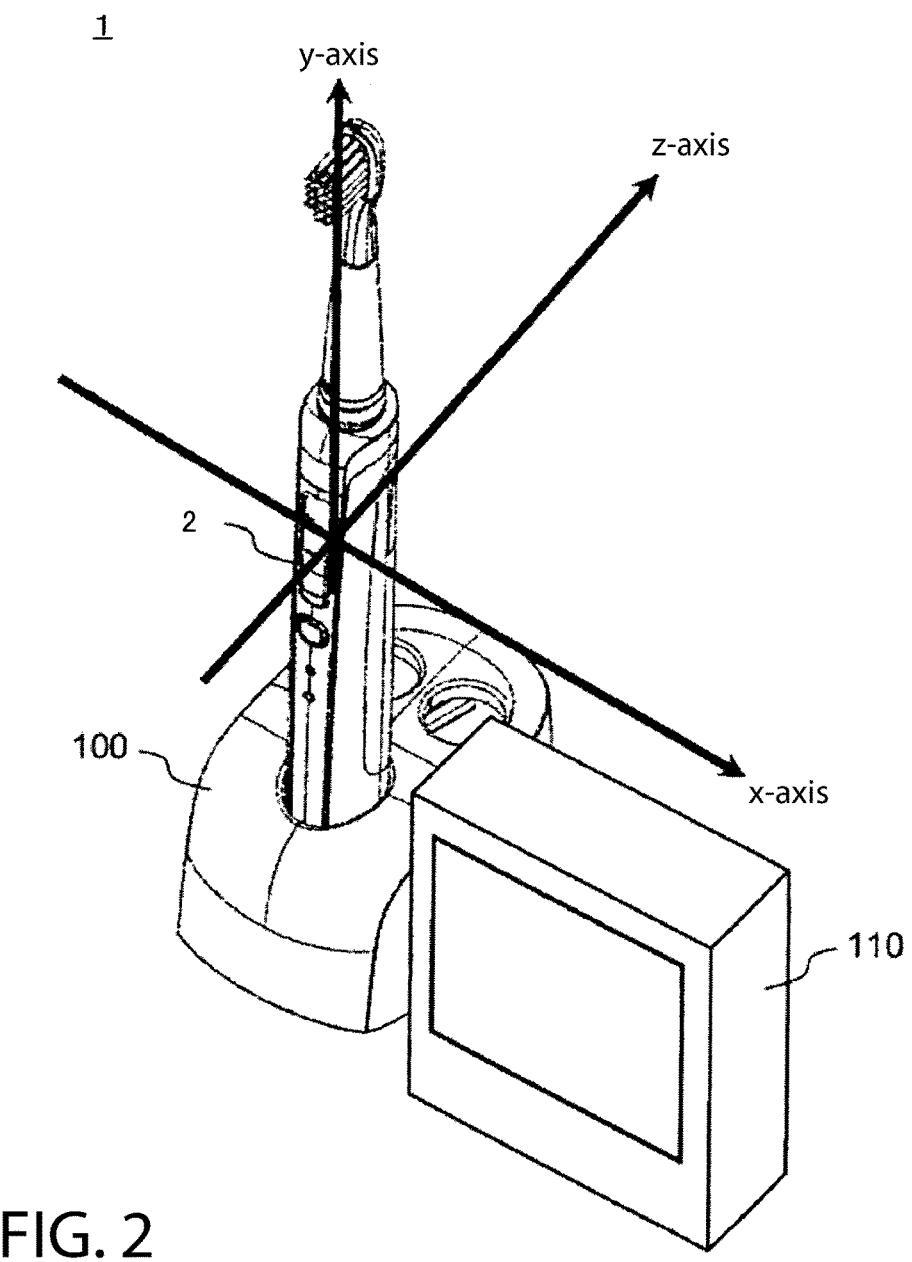
FIG. 2 is a perspective view illustrating an external appearance of the electric toothbrush device of FIG. 1.
Figure 3:
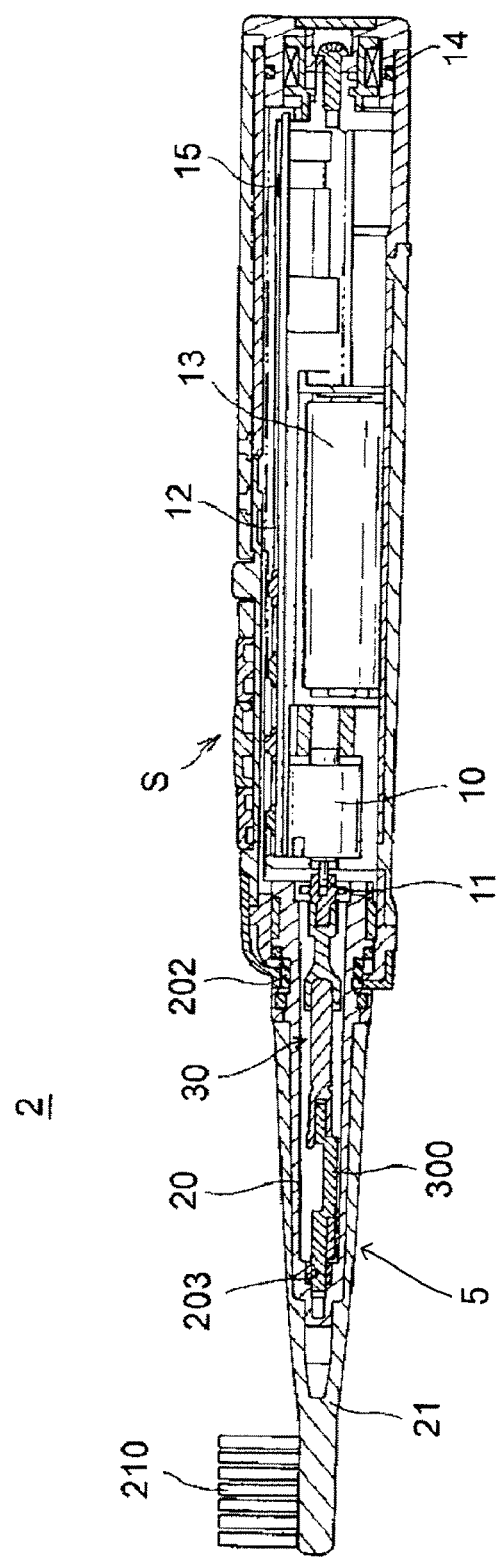
FIG. 3 is a cross section view illustrating an internal configuration of the electric toothbrush of FIG. 1.

FIG. 1 illustrates an example configuration of an electric toothbrush for describing an embodiment, FIG. 2 illustrates an external appearance of the electric toothbrush device of FIG. 1, and FIG. 3 illustrates an internal configuration of the electric toothbrush of FIG. 1.

The exemplified electric toothbrush device illustrated in FIG. 1 and FIG. 2 includes a main body 2 that has a brush 5 that oscillates by the drive of a built in motor 10, wherein the motor 10 that is the drive source is placed in the main body 2, a charger 100 for charging the main body 2, and a display unit 110 for outputting the brushing result.

In this embodiment, the main body 2 is roughly a cylindrical shape, and also serves as a handle part for the user to grip by hand when brushing the teeth. In the main body 2, a switch S is provided for carrying out switching of power on/off. Furthermore, a motor 10 that is the drive source, a drive circuit 12, a rechargeable battery 13 that is the power source, and a coil 14 for recharging is provided in the interior of the main body 2. When charging the rechargeable battery 13, by simply placing the main body 2 on the charger 100, it is possible to charge without contacting by electromagnetic induction. The drive circuit 12 has a central processing unit (CPU) 120 of executing various calculations and control, a memory 121 for storing programs and various setting values, a timer 122, a data transmission module 123 and the like. The data transmission module 123 carries out wireless communication with the data receiving module 112 of the display unit 110. The display unit 110 includes a display 111 for outputting data such as the brushing results received by the data receiving module 112.

Furthermore, in the interior of the main body, for example, an acceleration sensor 15 of multiple axes (here, the three axes x, y, z), an angular velocity sensor 16 of multiple axes (here, the three axes x, y, z) and geomagnetic sensor 17 of multiple axes (here, the three axes x, y, z), are provided for sensing the trajectory of movement and the three-dimensional attitude of the brush 5.

The acceleration sensor 15 is disposed so that the x-axis is parallel with respect to the brush surface, the y-axis coincides with the longitudinal direction of the main body 2, and the z-axis is perpendicular to the brush surface. In other words, when the main body is placed in the charger 100, the gravitational acceleration vector is parallel to the y-axis; when the brush surface is facing upwards, the gravitational acceleration vector is parallel to the z-axis; and when the brush surface is facing to the back, the gravitational acceleration vector is parallel to the x-axis. The output of each axis of the acceleration sensor 15 is input to the CPU 120, and employed for detecting the trajectory of movement and the attitude of the brush 5. A piezoresistive type, a capacitance type, or a MEMS sensor of a thermal sensing type is preferably employed as the acceleration sensor 15. Since the MEMS sensor is very small, it can easily be incorporated into the interior of the body 2. However, the format of the acceleration sensor 15 is not limited to this, but a sensor such as an electrodynamic type, strain gauge type, or piezoelectric may be employed.

The angular velocity sensor 16 is disposed so that it can detect the angular velocity around the x-axis, the angular velocity around the y-axis, and the angular velocity around the z-axis. The output of each axis out the angular velocity sensor 16 in input to the CPU 120, and employed for detecting the trajectory of movement and the attitude of the brush 5. Any type of sensor such as an oscillation type, optical type, and mechanical type may be used as the angular velocity sensor 16, but a MEMS sensor can appropriately be used since it is small and can easily be incorporated in main body 2.

The geomagnetic sensor 17 is disposed so that it can detect geomagnetism in the x-axis direction, the y-axis direction, and the z-axis direction. The output of each axis of the geomagnetic sensor 17 is input to the CPU 120, and employed for detecting the trajectory of movement and the attitude of the brush 5. A MEMS sensor such as a MR (Magneto-resistive) element type, MO (Magneto-Impedance) element type, and a hole element type is preferably employed as the geomagnetic sensor 17. The sensors discussed above can be used to detect a trajectory or attitude. Accordingly, these sensors (together or alone, depending on the embodiment) may be referred to as a "trajectory detecting module" and/or an "attitude detecting module." In other embodiments, other devices can be used to detect trajectory or attitude.

Furthermore, a load sensor 18 for sensing the brush pressure (load acting on the brush) is included in the interior of the main body 2. Although any type such as a strain gauge, a load cell, or a pressure sensor can be used, a MEMS sensor can be appropriately used as the load sensor 18 since it is small and can be easily incorporated in the main body 2.

The brush 5 includes a stem part 20 fixed to the main body 2 side, and a brush component 21 mounted on the stem part 20. Brush bristles 210 are attached to the top portion of the brush component 21. Since the brush component 21 has consumable parts, it is configured to be freely detachable with respect to the stem part 20 so that it can be replaced with a new one.

In this embodiment, the stem part 20 is made from a resin material, and attached to the main body 2 via an elastic member 202 made from an elastomer. The stem part 20 is a cylindrical member in which the tip (tip end of the brush side) is closed, and has a bearing 203 in the tip end of the interior of the tube. The tip of the eccentric shaft 30 connected to the rotary shaft 11 of the motor 10 is inserted into the bearing 203 of the stem part 20. The eccentric shaft 30 has a weight 300 near the bearing 203, and the center of gravity of the eccentric shaft 20 is shifted from the center of rotation. Note that a minute clearance is provided between the tip of the eccentric shaft 30 and the bearing 203.

In this embodiment, the CPU 120 is provided in the motor 10, and rotates the rotary shaft 11 of the motor 10. Although the eccentric shaft 13 also rotates along the rotation of the rotary shaft 11, the eccentric shaft 30 carries out the movement such as turning about the axis of rotation since the center of gravity is shifted. Thus, the tip of the eccentric shaft 30 repeatedly collides against the inner wall of the bearing 203, and the stem part 20 and the brush component 21 mounted thereon oscillates (moves) at high speed. That is, the motor 10 plays a role of the drive module for oscillating (moving) the brush 5 and the eccentric shaft 30 plays a role of a movement transmission mechanism (movement conversion mechanism) for converting the output (rotation) of the motor 10 to oscillation of the brush 5.

The user can carry out brushing by applying the hand of the main body 2, that is, the brush bristles 210 for oscillating at high speed, to the teeth. Note that, the CPU 210 monitors the continuous operation time by using the timer 122, and automatically stops the oscillation of the brush 5 after a predetermined amount of time (for example, 2 minutes) has elapsed.

The way food residue and plaque are attached is different at each site, therefore the effective brushing operation is different at each site. Thus, it is preferable to carry out an evaluation at each site of whether or not appropriate brushing is being carried out. Therefore, the electric toothbrush device 1 performs a brushing evaluation of each site by estimating the brushing site based on the trajectory of movement and the attitude of the brush 5, by using an acceleration sensor 15, angular velocity sensor 16, and a geomagnetic sensor 17. Various evaluation items are considered, but here an evaluation of three items, the brushing time, brush angle, and brush pressure, is carried out.

Figure 4:
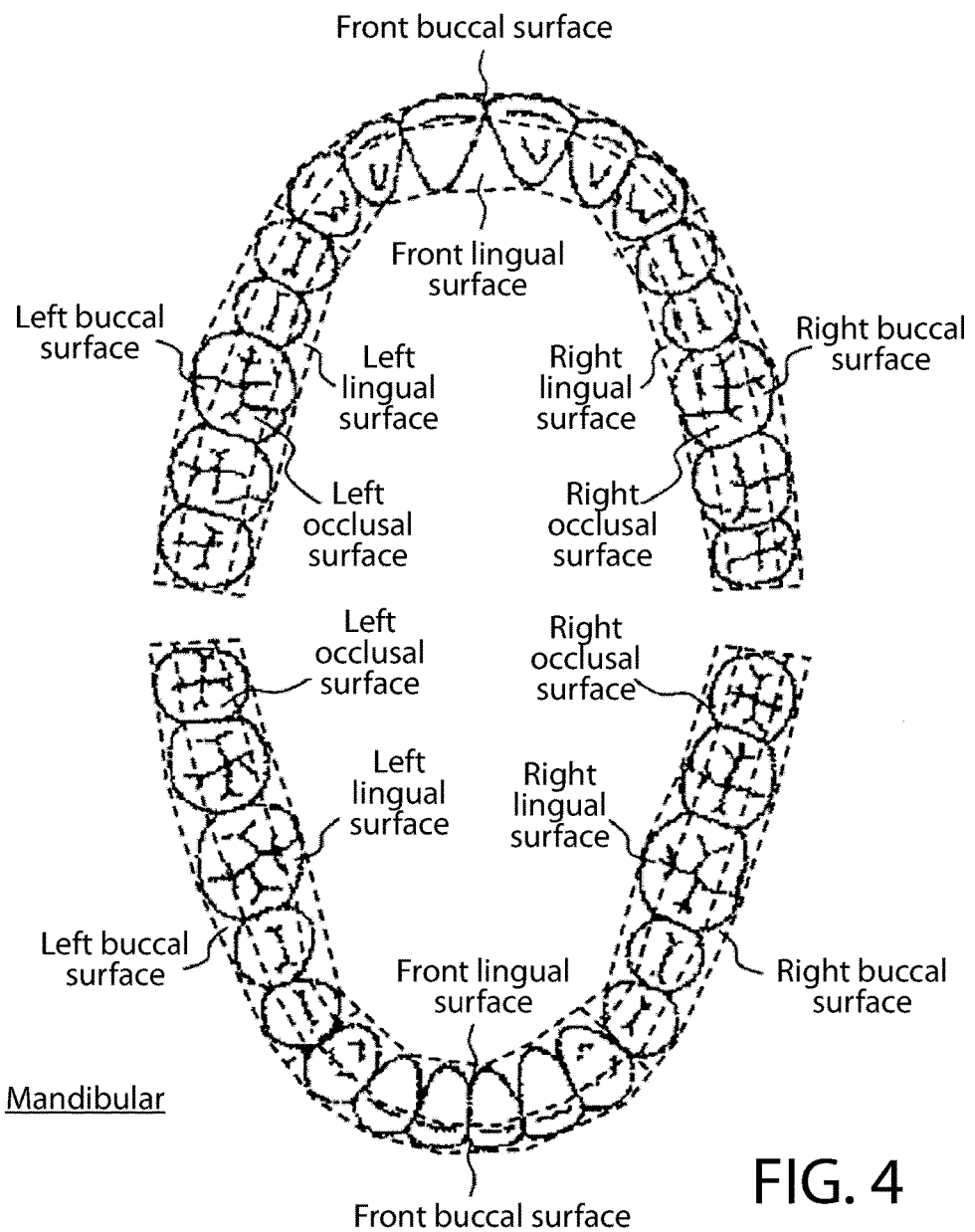
FIG. 4 is a diagram illustrating the division of brushing sites.

As illustrated in FIG. 4, the upper and lower teeth surfaces are divided into 16 sections of a "maxillary front buccal surface", "maxillary front lingual surface", "maxillary left buccal surface", "maxillary left lingual surface", "maxillary left occlusal surface", "maxillary right buccal surface", "maxillary right lingual surface", "maxillary right occlusal surface", "mandibular front buccal surface", "mandibular front lingual surface", "mandibular left buccal surface", "mandibular left lingual surface", "mandibular left occlusal surface", "mandibular right buccal surface", "mandibular right lingual surface", and a "mandibular occlusal surface". However, division of the teeth surface is not limited to this, and may be divided into a rougher division or a finer division.

Figure 5:
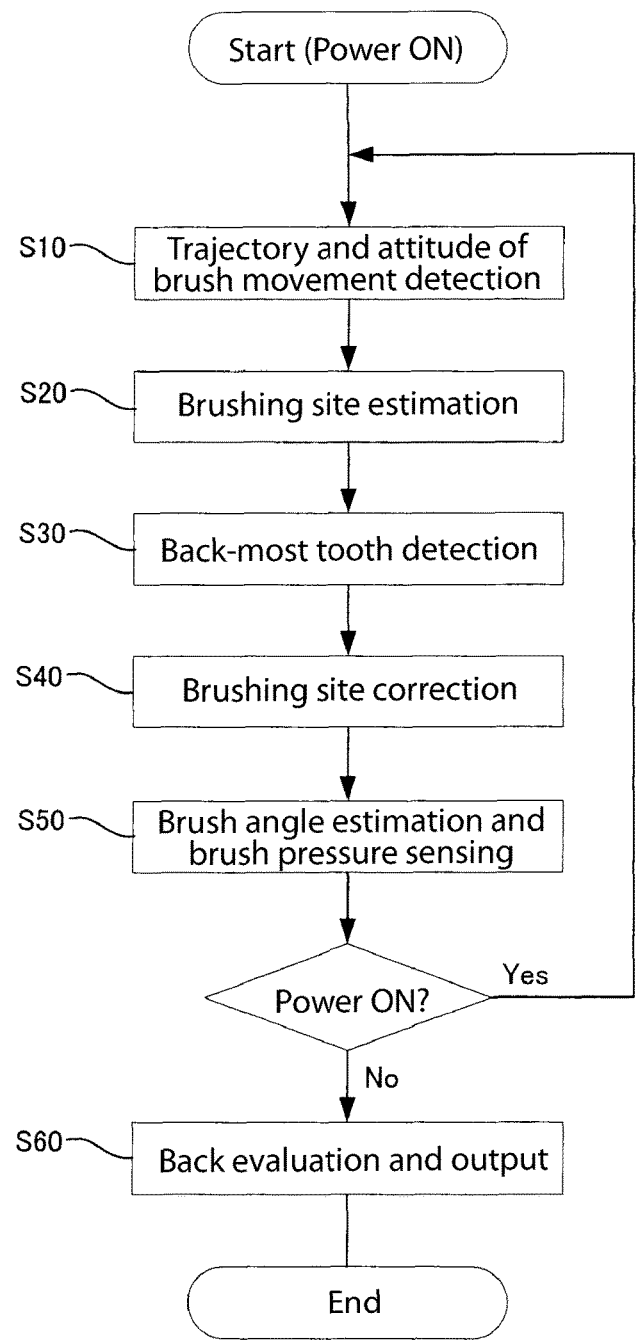
FIG. 5 is a flow chart illustrating an example of the brushing evaluating process.

The flow of the brushing evaluation will be described specifically with reference to FIG. 5. Note that, the process described hereafter is a process performed according to the program stored in the memory 121 of the CPU 120, unless otherwise stated.

When the power supply of the main body is ON, the CPU 120 detects the trajectory of movement and the attitude of the brush 5 based on the output of the acceleration sensor 15, the angular velocity sensor 16, and the geomagnetic sensor 17 (Step S10). Then, the CPU 120 estimates the brushing site by using the trajectory detected by at least step S10 (Step S20). Then, the CPU 120 carries out detection of the back most tooth when the brushing site estimated by step S20 is the back side site of the teeth rows end (Step S30). Then, the CPU 120 corrects the brushing site of each position in the trajectory of movement of the brush 5 based on the position of the back most tooth detected by step S30 (Step S40). Then, the CPU 120 carries out estimation of the brush angle and sensing of the brush pressure (Step S50). The information of the brushing site, the brush angle and the brush pressure is recorded in the memory 121 associated with a position in the trajectory of the brush 5.

The process of steps S10 to S50 are repeatedly performed, when the power supply is turned OFF or the continuous operation time reaches a predetermined time (for example 2 minutes), the brushing results at each site are evaluated based on brushing information (brushing site, brush angle, brush pressure) recorded in the memory 121, and outputs the evaluation results to the display unit 110 (Step S60).

Hereinafter, the process of step S10 to S60 will be described in detail.

The CPU 120 acquires outputs Ax, Ay and Az of the x-axis, y-axis and z-axis respectively, from the acceleration sensor 15; acquires outputs Bx, By and Bz of the x-axis, y-axis and z-axis respectively, from the angular velocity sensor 16; and acquires outputs Cx, Cy and Cz of the x-axis, y-axis and z-axis respectively, from the geomagnetic sensor 17. Ax displays the acceleration component of the x-axis direction, Ay displays the acceleration component of the y-axis direction, and Az displays the acceleration component of the z-axis direction. Bx displays the angular velocity component about the x-axis, By displays the angular velocity component about the y-axis, Bz displays the angular velocity component about the z-axis. Cx displays the magnetic component of the x-axis direction, Cy displays the magnetic component of the y-axis direction, Cz displays the magnetic component of the z-axis direction.

When the size of the resultant vector A (Ax, Ay, Az) is smaller than a predetermined threshold value equivalent to the gravitational acceleration, the CPU 120 determines that the main body 2 is stationary, and the output Ax, Ay and Az of the acceleration sensor 15 is made to be the attitude vector D (Dx, Dy, Dz) for displaying a three dimensional attitude of the brush.

When the size of the resultant vector A (Ax, Ay, Az) is greater than the threshold value, the CPU 120 determines that the main body 120 is moving. The angular variation amount of the main body 2 is obtained about each axis of the x-axis, y-axis and z-axis from when the main body 2 was most recently determined to be stationary. Based on the outputs Bx, By and Bz of the angular velocity sensor, rotated at the angular variation amount for obtaining a resultant vector A (Ax, Ay, Az) of when the main body 2 was most recently determined to be stationary, the attitude vector D (Dx, Dy Dz) is obtained.

The attitude vector D (Dx, Dy, Dz) obtained as above, corresponds to the gravitational acceleration. Note that the angular velocity sensor 16 generally results in drift, and after the error in calculation of the angular velocity amount is accumulated, the CPU 120 carries out a zero calibration of the angular velocity sensor 16 from time to time by using output of the acceleration sensor 15 and the geomagnetic sensor 17.

Furthermore, the CPU 120 obtains the variation amount of each axis direction of the x-axis, y-axis and z-axis, based on the acceleration component obtained by removing the gravitational component from the output Ax, Ay and Az of the acceleration sensor 15. The gravitational acceleration included in the outputs Ax, Ay and Az can use the attitude vector D (Dx, Dy, Dz). Also, the CPU 120 obtains the trajectory of the movement of the brush 5 by taking into consideration the position of the brush 5 in the main body 2 that is determined from the three dimensional attitude of the brush 5.

The CPU 120 estimates the brushing site at each position on the trajectory of movement of the brush 5 by carrying out matching of the trajectory of movement of the brush 5 and the teeth row surface. (In this regard, the CPU 120 is sometimes referred to as a "site estimating module," though other processors can be used to estimate a site.) Although the estimation accuracy of the brushing sites increases as the trajectory is accumulated, if the starting site of brushing is reported to the user, it is possible to accurately carry out estimation of the brushing site from a relatively early stage.

Figure 6:
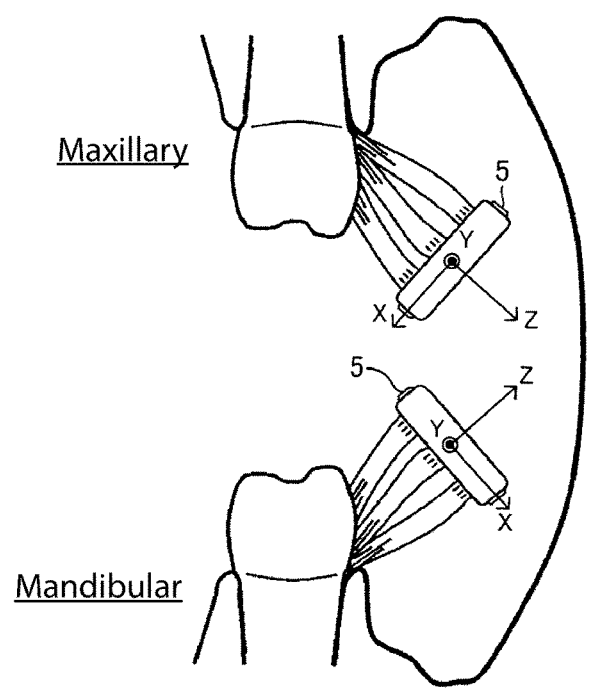
FIG. 6 is a diagram illustrating an example of the estimating method of brushing sites based on the attitude of the brush.

Note that, by taking this into consideration together with the attitude of the brush 5, it is possible to estimate the brushing site with a higher accuracy. For example, it is possible to determine whether it is the maxillary or the mandibular based on the z-axis direction component Dz of the attitude vector D. As illustrated in FIG. 6, it is noted that when brushing the maxillary teeth, the brushing surface faces considerably upwards, and when brushing the mandibular teeth, the brush surface faces considerably downwards, and it is possible to detect that when Dz>0 it is the maxillary, and when Dz≤0 it is the mandibular.

When the estimated brushing site is the back side site of the teeth row ends, that is, the "maxillary left buccal surface", "maxillary left lingual surface", "maxillary left occlusal surface", "maxillary right buccal surface", "maxillary right lingual surface", "maxillary right occlusal surface", "mandibular left buccal surface", "mandibular left lingual surface", "mandibular left occlusal surface", "mandibular right buccal surface", "mandibular right lingual surface", and a "mandibular occlusal surface", the CPU 120 carries out detection of the back most tooth. (In this regard, the CPU 120 is sometimes referred to as a "back most tooth detecting module," though other processors can be used in detecting a back most tooth.)

Figure 7:
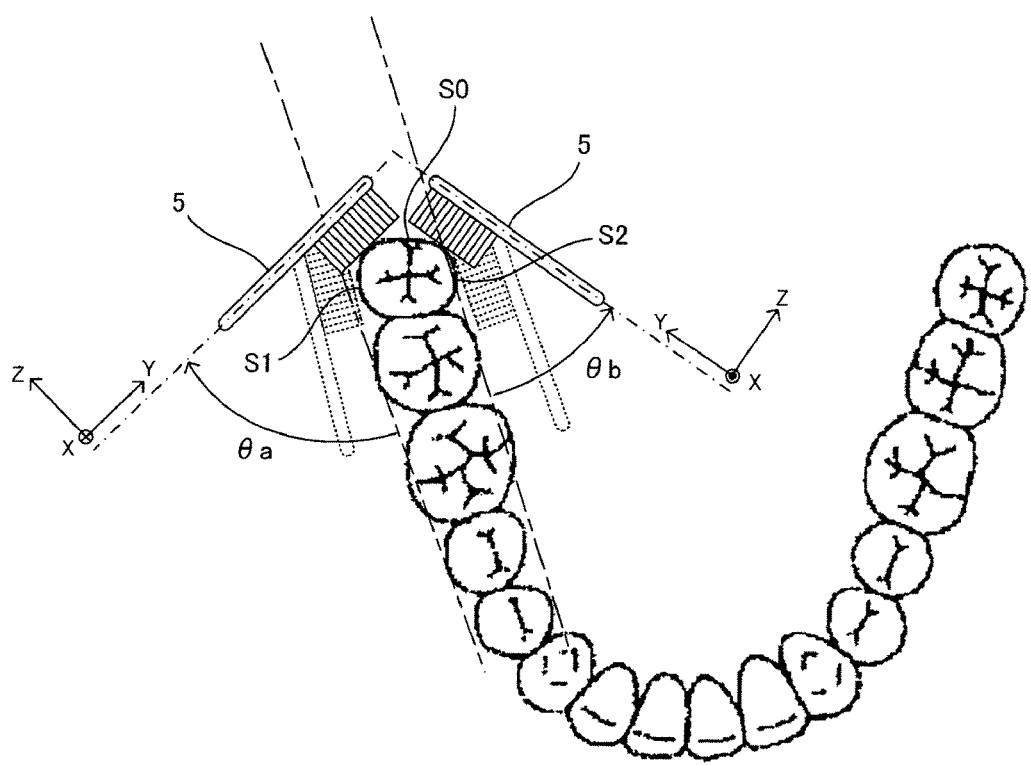
FIG. 7 is a diagram illustrating an example of the detecting method of the back most tooth based on the attitude of the brush.
Figure 8:
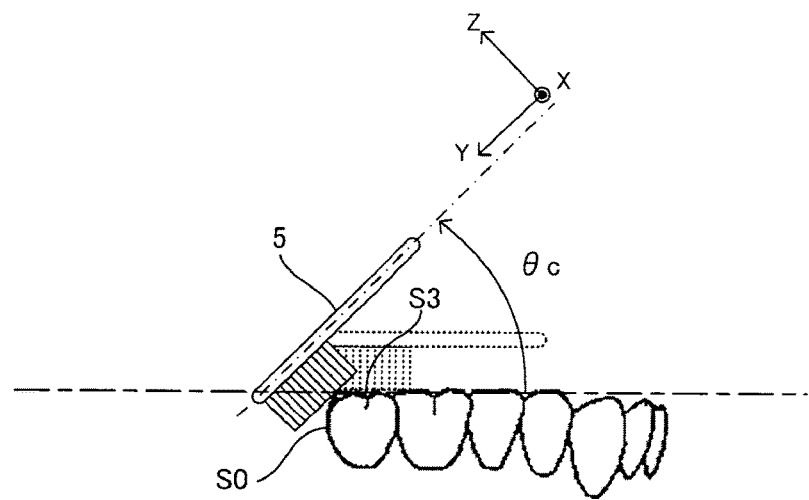
FIG. 8 is a diagram illustrating another example of the detecting method of the back most tooth based on the attitude of the brush.

FIG. 7 illustrates and example of a detection method of the back most tooth when the estimated brushing site is the "mandibular left buccal surface" and the "mandibular left lingual surface", and FIG. 8 illustrates and example of a detection method of the back most tooth when the estimated brushing site is the "mandibular left occlusal surface".

When brushing the side surface S0 of the maxillary left back most tooth, typically, the brush 5 reaches the side surface S0 of the back most tooth by moving to the back side along the mandibular left teeth row ends.

When the brush 5 is moved along the "mandibular left buccal surface" for example, the brush 5 rapidly rotates about the x-axis in a process leading to the side surface S0 from the buccal surface S1 of the back most tooth, as illustrated in FIG. 7. There, when the estimated brushing site is the "mandibular left buccal surface", and when the variation amount θa of the attitude about the x-axis of the brush 5 is greater than a predetermined threshold value on the basis of the attitude of the brush 5 along the teeth row ends of the "mandibular left buccal surface", it is possible to detect the back most tooth. The attitude of the brush 5 along the teeth row surface of the mandibular left buccal surface that serves as a reference, for example, can be an average of the attitude of the brush 5 at each position estimated as the "mandibular left buccal surface" in the trajectory of the brush 5.

When the brush 5 moves along the "mandibular left lingual surface", the brush 5 rapidly rotates about the x-axis in a process leading to the side surface S0 from the back most tooth lingual surface S2. There, when the estimated brushing site is the "mandibular left lingual surface", and when the variation amount θb of the attitude about the x-axis of the brush 5 is greater than a predetermined threshold value on the basis of the attitude of the brush 5 along the teeth row ends of the "mandibular left lingual surface" and on the basis of the attitude of the brush 5, it is possible to detect the back most tooth.

Furthermore, when the brush 5 moves along the "mandibular left occlusal surface", the brush 5 rapidly rotates about the x-axis in a process leading to the side surface S0 from the back most tooth occlusal surface S3, as illustrated in FIG. 8. There, when the estimated brushing site is the "mandibular left occlusal surface", and when the variation amount θc of the attitude about the x-axis of the brush 5 is greater than a predetermined threshold value on the basis of the attitude of the brush 5 along the teeth row ends of the "mandibular left occlusal surface", it is possible to detect the back most tooth.

When the estimate brushing site is the "mandibular right buccal surface", "mandibular right lingual surface", "maxillary left buccal surface", "maxillary left lingual surface", "maxillary right buccal surface", and the "maxillary right lingual surface", in the same manner as the detection method in FIG. 7, and furthermore, when the brushing site is the "mandibular right occlusal surface", "maxillary left occlusal surface", and the "maxillary right occlusal surface", in the same manner as the detection method illustrated in FIG. 8, it is possible to detect the back most tooth based on the variation of attitude of the brush 5.

Figure 9:
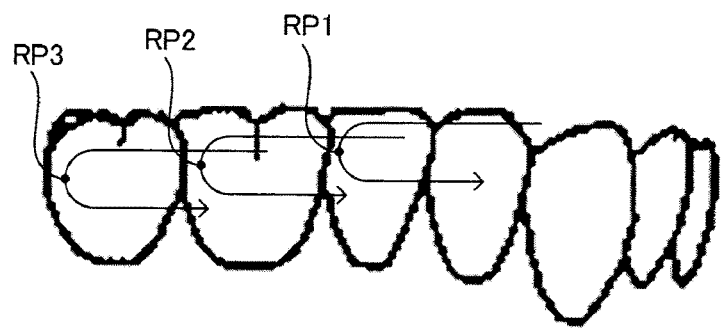
FIG. 9 is a diagram illustrating an example of the detecting method of the back most tooth based on the trajectory of movement of the brush.

The detection of the back most tooth above focuses on the three dimensional attitude of a specific brush 5 in brushing of the back most tooth, but the detection method of the back most tooth illustrated in FIG. 9 focuses on the movement of a specific brush 5 in brushing of the back most tooth.

Normally, it is difficult to move the brush 5 to the back most tooth along the teeth row ends due to interference of biological tissue in the mouth. Furthermore, after the brush 5 reaches the back most tooth by moving to the teeth side along the teeth row ends, the brush 5 is moved again to the front side. There, as illustrated in FIG. 9, in the trajectory portion of the back side portion of the teeth row ends of among the trajectory of movements of the brush 5, and of among a return point RP1, RP2, and RP3 of movement of the brush 5, it is possible to detect the return point RP3 of the movement of the brush 5 in the back most tooth as the back most tooth. Note that, the trajectory portion of the "mandibular left buccal surface" in FIG. 9 is illustrated, but even for trajectory portions of another back side portion, a returning point of the movement of the brush 5 in the same back most tooth can be detected as the back most tooth.

The CPU 120 is configured so as to detect the back row teeth by independently carrying out detection of the back most tooth based on variation of the attitude of the brush 5 above, detection of the back most tooth based on the trajectory of the brush 5 respectively, and preferably is configured so as to detect the back most tooth based on variation of the attitude of the brush 5 at the returning point of the back most side of movement of the brush 5. Thus, it is possible to further increases the detection accuracy of the back most tooth.

Figure 10:
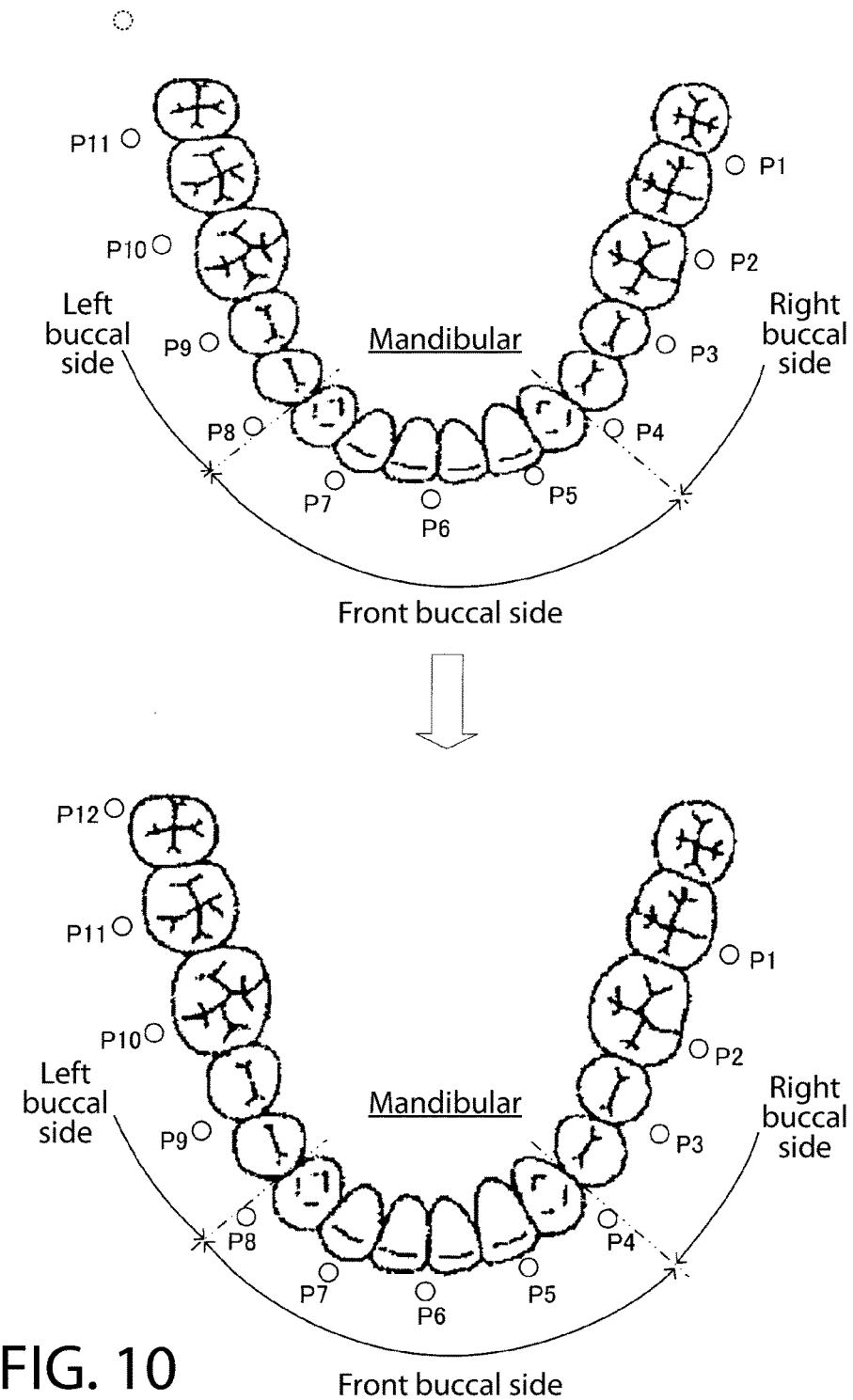
FIG. 10 is a diagram illustrating an example of the correcting process of brushing sites.

FIG. 10 illustrates an example of a correction process of the brushing sites at each position on the trajectory of movement of the brush 5.

For each position P1 to P11 on the trajectory of movement of the brush 5, the brushing sites of brush position P1 to P4 is estimated as the "mandibular right buccal surface", the brushing sites P5 to P7 are estimated as the "mandibular front buccal surface", and the brushing sites P8 to P11 are estimated as the "mandibular left buccal surface". Also, for position P12 of the brush 5 detected by the following step S10, the brushing site is estimated as the "mandibular left buccal surface, and the back most tooth is detected in the position P12.

The CPU 120 updates the position of the mandibular left back most tooth to position P12 in the trajectory of movement of the brush 5 when the back most tooth are detected by position P12. Also, the CPU 120 corrects the brushing site of each position P1 to P11 estimated by the matching of the teeth row ends and the trajectory of movement of the brush 5, based on the position of the updated back most tooth. In the example illustrated, due to the correction, P1 to P3 are corrected to the "mandibular right buccal surface", P4 to P8 are corrected to the "mandibular front buccal surface", and P9 to P11 are corrected to the "mandibular left buccal surface".

Thus, when the back most tooth is detected, the position of the back most tooth in the trajectory of movement of the brush 5 accumulated to that point, can further increase the estimation accuracy of the brushing site by matching of the teeth row ends and the following trajectory, due to correcting the brushing site at each position in the trajectory based on the position of the updated back most tooth.

Figure 11:
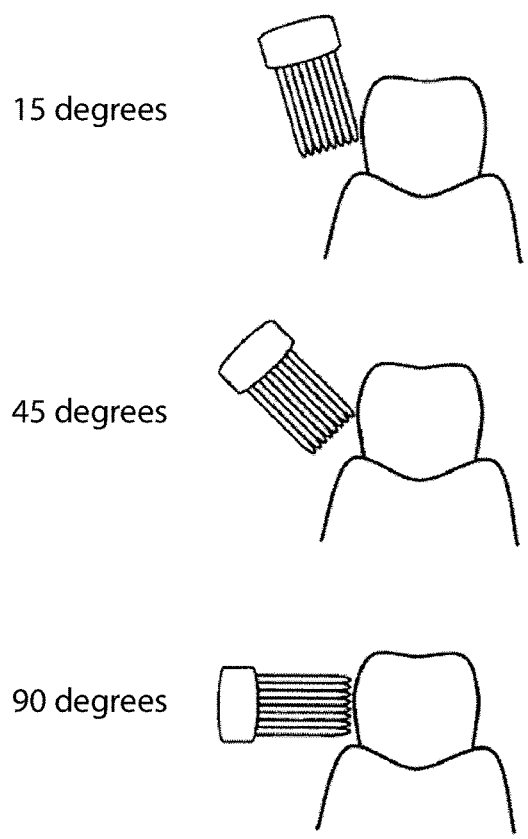
FIG. 11 is a diagram for describing the brush angle.

The CPU 120 estimates the brush angle based on the attitude of the brush 5 detected by step S10. The brush angle is the angle per brush against the tooth axis (axis along the head and root of the tooth). The upper part of FIG. 11 illustrates a state in which the brush angle=15 degrees, the middle part illustrates a state in which the brush angle=45 degrees, and the lower part illustrates a state in which the brush angle=90 degrees. When effectively scraping out food residue and plaque from between the teeth and the periodontal pockets, the bristles of the brush may move the brush so as to enter between the teeth and the periodontal pockets. Therefore, a brush angle in the range of 35 degrees to 55 degrees is preferred.

The brush angle, for example, can be estimated from the z-axis direction component Dz of the attitude vector D; when the brush angle is about 90 degrees Dz will be about 0, and as the brush angle decreases the absolute value of Dz increases, which is because the value of Dz changes significantly corresponding to the brush angle. The brush angle may be calculated in a continuous quantity, or it may be a rough estimate such as "less than 35 degrees", "35 to 55 degrees", and "55 degrees or above".

Furthermore, the CPU 120 calculates the brush pressure based on the output of the load sensor 18. When the brush pressure is too mall the plaque removal power decreases, and conversely, when it is too large there is a possibility of problems such as a decrease in the brush life and an increased burden on the gums occurring. Since the brush pressure of an electric toothbrush may be less than a normal toothbrush, most people who started using an electric toothbrush said there was a tendency of excessive brush pressure. The optimum value of brush pressure is about 100 g.

The CPU 120 evaluates the brushing results of each site based on the brushing information (brushing site, brush angle, brush pressure) of each position in the trajectory of movement of the brush 5 recorded in the memory 121, and outputs the evaluation results to the display unit 110 (Display 111). Here, an evaluation of the brushing time, brush angle, and brush pressure are carried out.

The brushing time of every site is counted by counting up every site of the brushing sites of each position in the trajectory of the brush 5. For example, if the process of step S10 to S50 is performed once for 0.1 seconds, each time the brushing site is counted up, the brushing time of the site is counted up by +0.1 seconds.

The brush angle of every site is aggregated at every site of the brush angle of each position based on the brushing site of each position in the trajectory of movement of the brush 5, and for example, is calculated as the average value. Likewise, the brush pressure of every site is aggregated at every site of the brush angle of each position based on the brushing site of each position in the trajectory of movement of the brush 5, and for example, is calculated as the average value.

The evaluation of the brushing time, brush angle, and brush pressure of every site is not particularly limited. The brushing time can be evaluated in three stages for example, 7 seconds is "insufficient", 7 seconds to 15 seconds is "good", and greater than 15 seconds is "excessive". Furthermore, the brush angle can be evaluated in three stages for example, "less than 35 degrees" is "insufficient", "35 degrees to 55 degrees" is "good", and "55 degrees or above" is "excessive". Furthermore, the brush pressure can be evaluated in three stages for example, less than 80 g is "insufficient", 80 g to 150 g is "good", and greater than 150 g is "excessive". These evaluation results are transmitted to the display unit 110.

Figure 12:
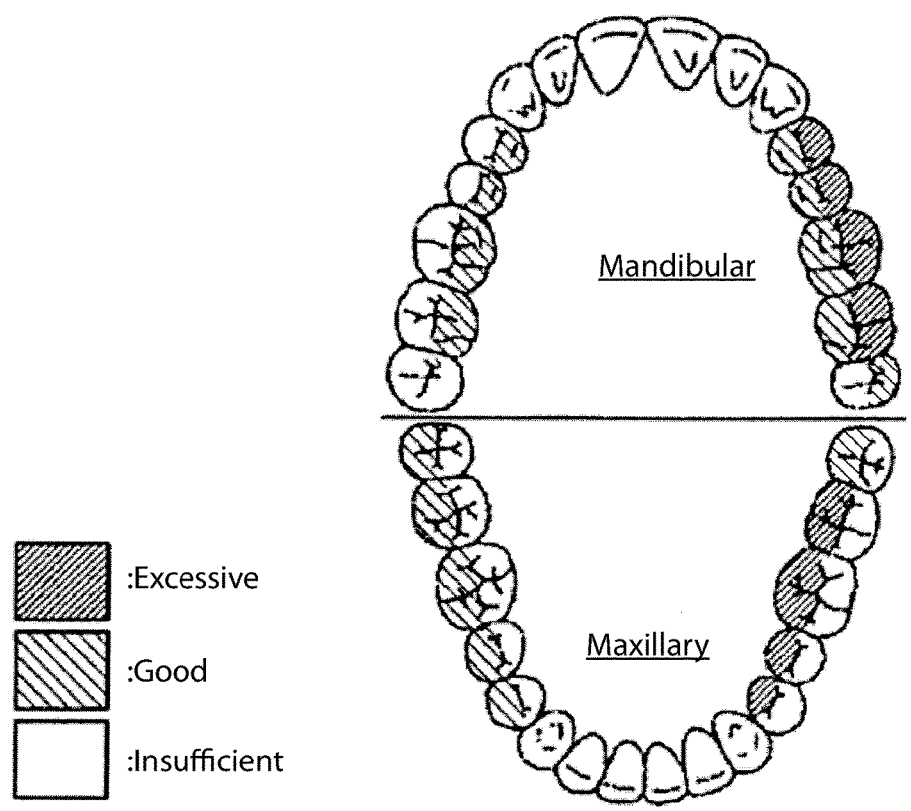
FIG. 12 is a diagram illustrating an example of outputting evaluation results of the brushing.

The output of the evaluation results in the display unit 110 are not particularly limited. For example, as illustrated in FIG. 12, the upper and lower teeth are displayed, and each site can be displayed by a color ("insufficient" is white, "good" is yellow, "excessive" is red, and the like) corresponding to the evaluation results of each site by seeing a display as such, the user can intuitively understand when the brushing of some site in a tooth row is insufficient or excessive.

Also, since the position of the back most tooth in the trajectory of movement of the brush 5 is detected, it is possible to evaluate the results of the brushing of the back most tooth as a detailed site of among the back side portion of the teeth row ends. The CPU 120 carries out an evaluation of whether or not the back most tooth was brushed based on the presence or absence of the detection of the back most tooth, and furthermore, an evaluation of the brushing time, brush angle, and brush pressure of the back most tooth based on the brush position that detected the back most tooth and the brushing information near that position. The back most tooth in which there is a tendency to leave un-brushed is detected, and by presenting the evaluation results regarding the brushing of the back most tooth to the user, it is possible to promote health of the teeth.

As described above, according to the electric toothbrush device 1, since it is possible to detect the back most tooth with an acceleration sensor 15 and the like for detecting the trajectory of movement and the attitude of the brush 5, the configuration of the electric toothbrush 1 can be made to be simple. Also, when the back most tooth is detected, the position of the back most tooth in the trajectory of movement of the brush 5 accumulated to that point are updated, and it is possible to accurately estimate the brushing site since the brushing site at each position in the trajectory is correct based on the position of the updated back most tooth.

Figure 13:
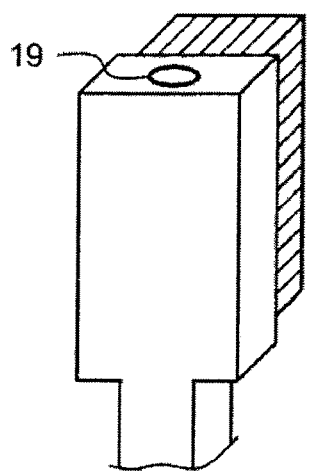
FIG. 13 is a diagram illustrating a variation of a configuration of the electric toothbrush device.

FIG. 13 illustrates a configuration of a variation of the electric toothbrush 1.

The example illustrated in FIG. 13 provides a camera 19 in the end of the y-axis direction of the brush 5. Any camera that can acquire image information in the mouth, such as a visible light camera or an infrared camera, can be employed as the camera 19. The infrared camera monitors the emitted heat (also referred to as thermography). Since the mouth can be dark while brushing, an infrared camera is more preferable than a visible light camera. Since the contour of the uvula may be understood as described below, the resolution of the camera may be not very high.

The CPU 120 acquires an image from the camera 19 in addition to the output of the acceleration sensor 15, angular velocity sensor 16, and geomagnetic sensor 17 in step S10 (FIG. 5), the uvula can be detected from the image. The detection of the uvula is possible using a well-known image analysis technique. For example, contour detection of the uvula by edge extraction or Hough transform, or detection of the uvula by pattern matching and the like is considered.

When the brush 5 is on the lingual side, there is a high probability that the uvula will appear in order for the end of the brush 5 to face towards the throat. On the other hand, when the brush 5 on the buccal side, the uvula does not appear in the image. Therefore, CPU 120 determines it to be "lingual" when the uvula is not detected, and as "buccal" when the uvula is detected.

Note that, although the uvula is the detected object, the attitude and position of the brush may be determined by recognizing other sites in the mouth (for example, tongue, throat, teeth, gums and the like). For example, if the tongue and throat appear in the image, it can be determined that the brush is in the lingual side.

Thus, in addition to the trajectory of movement of the brush 5 detected based on the output of the acceleration sensor 15, angular velocity sensor 16, and geomagnetic sensor 17, by complementarily using the image of the camera 19 in estimation of the brushing site, it is possible to further increase the estimation accuracy of the brushing site.

Note that, a light sensor provided in the brush portion is preferable to a camera. Since light is detected in the lingual side whereas the buccal side is completely dark, it is possible to determine both by analyzing the output of the light sensor.

The embodiments described herein are in all respects examples and are in no way considered to be limited thereto. The scope of the present invention is indicated by the scope of the patent claims and is intended to include all alternatives within equivalent meaning and scope to the patent claims.

As described above, the following matters are disclosed in the present specification. The disclosed electric toothbrush includes: a trajectory detecting module for detecting the trajectory of movement of a brush; an attitude detecting module for detecting the attitude of the brush; a site estimating module for estimating the brushing site at each position in the trajectory, using a trajectory detected by at least the trajectory detecting module; and a back most tooth detecting module for detecting the back most tooth based on change of attitude detected by the attitude detecting module, wherein the site estimating module updates the position of the back most tooth in the trajectory detected by the trajectory detecting module, when the back most tooth is detected by the back most tooth detecting module, and corrects the brushing sites at each position on the trajectory based on the position of the updated back most tooth.

Furthermore, in the disclosed electric toothbrush device, the back most tooth detecting module, in reference to the attitude of the brush along the teeth row surface of the back side site, detects the back most tooth based on a difference between the reference of attitude detected by the attitude detecting module.

Furthermore, in the disclosed electric toothbrush device, the back most tooth detecting module detects the returning point at the back most side of movement of the brush as the back most tooth, in the trajectory portion in which the brushing site estimated by the site estimation module of among the trajectory detected by the trajectory detecting module is the back side site of the teeth row end.

Furthermore, in the disclosed electric toothbrush device, the site estimation module further uses an attitude detected by the attitude detecting module, and estimates the brushing site at each site on the trajectory detected by the trajectory detecting module.

Furthermore, the disclosed electric toothbrush device further comprises an evaluation output module for evaluating and outputting brushing results of every site.

Section II

A brushing site can be estimated based on the detection signal of an acceleration sensor, but the accuracy of such a method can be insufficient. For example, when a user moves his face and the electric toothbrush together in the state of inserting a brush unit into his mouth, although the tooth that the brush unit is contacting does not change, a change occurs in the detection signal of the acceleration sensor. Because of this, there is a possibility that the brushing site can be estimated falsely.

Furthermore, when the user moves only his face in the state of inserting the brush unit into his mouth, although a change does not occur in the detection signal of the acceleration sensor, the tooth that the brush unit is contacting changes. Because of this, there is a possibility that the brushing site can be estimated falsely. Accordingly, there is need to address such issues to provide improved brushing site estimation accuracy.

The electric toothbrush of the present invention is provided with a driving module that oscillates the brush unit, an acceleration sensor, a first signal achieved from a frequency of a first threshold or more from the output signal of the acceleration sensor, a signal extraction module that extracts a second signal achieved from a frequency of a second threshold or less, a brushing site estimation module by the brush unit based on the output signal of the acceleration sensor, and a correction module that corrects the brushing site estimated by the brushing site estimation module based on the amplitude of the first signal and the amplitude of the second signal.

The brushing site estimation method of the present invention is a brushing site estimation method by the electric toothbrush having the driving module that oscillates the brush unit and the acceleration sensor and is provided with a signal extraction step that extracts the first signal achieved from the frequency of the first threshold or more and the second signal achieved from the frequency of the second threshold or less, a brushing site estimation step that estimates the brushing site by the brush unit based on the output signals of the acceleration sensor, and a correction step that corrects the brushing site estimated by the brushing site estimation step.

Figure 14:
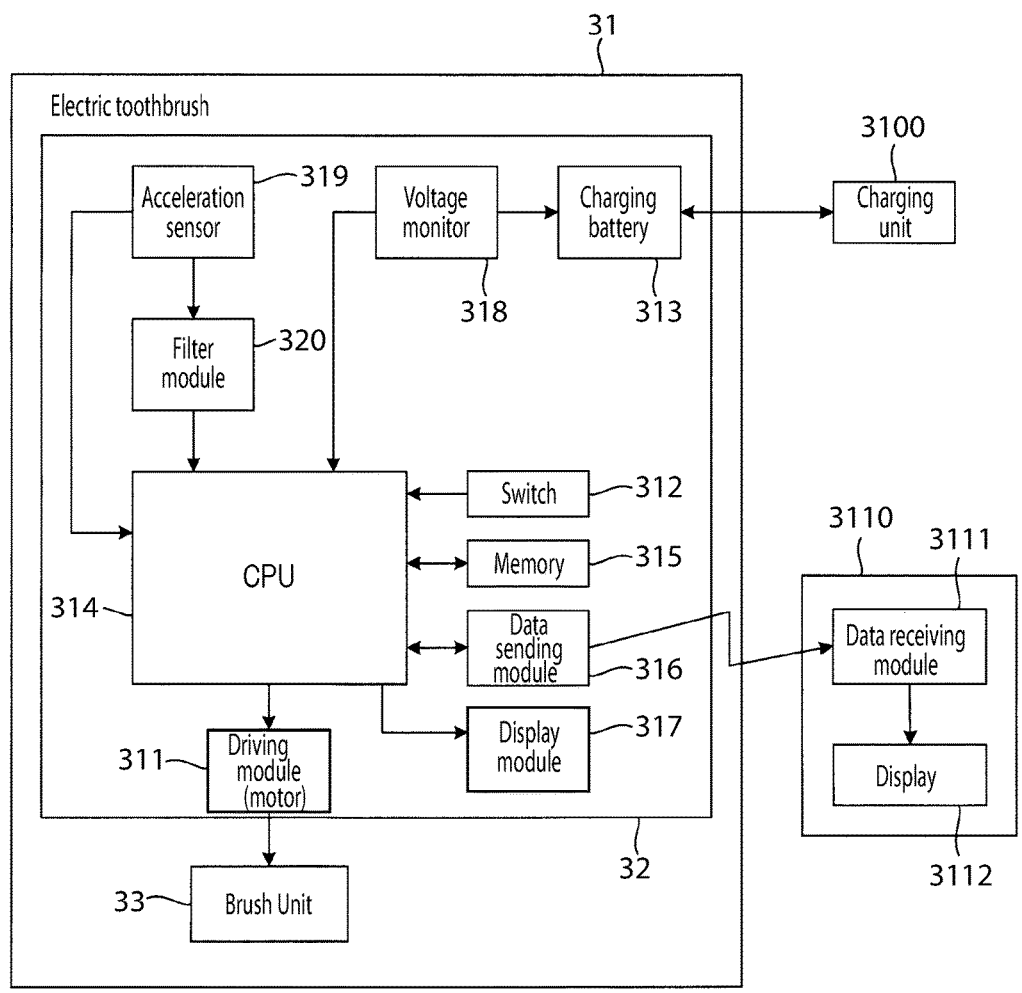
FIG. 14 is a schematic of a brushing support system according to an embodiment.

FIG. 14 is a diagram illustrating the schematic structure of the brushing support system for describing an embodiment of the present invention. This system is provided with an electric toothbrush 31, a charging unit 3100, and a display unit 3110.

The electric toothbrush 31 is provided with a main body 32 having a motor 311 built in as a driving module that oscillates a brush unit 33, and the brush unit 33 that oscillates by the driving of the motor 311.

The main body mainly exhibits a cylindrical shape and also has a handle portion for the user to grasp with their hand when brushing teeth. The brush unit 3 has a brush portion arranged by a plurality of brush groups bundling several hairs, and has a detachable structure to a main body 32.

A switch 312 for performing a power on/power off is provided on the main body 32 of the electric toothbrush 31.

The motor 311 (for example, a direct current motor), a charging battery 313 that is the power source for supplying electricity to each portion, a CPU (Central Processing Unit) 314, and the like are provided on the inner portion of the main body 32 of the electric toothbrush 31.

The CPU 314 carries out each type of calculation and control. A memory 315, a data sending module 316, a display module 317, and the like are connected to the CPU 314. The memory 315 houses a program, each type of set value, and the like. The data sending module 316 performs wireless communication between a data receiving module 3111 of the display unit 3110. The display unit 317 displays the brushing effect and the like.

A voltage monitor 318 for detecting the output voltage (the remaining battery) of the charging battery 313, an acceleration sensor 319 for sensing the attitude of the electric toothbrush 31, and a filter module 320 that filter processes the output signal of the acceleration sensor 319 are further provided on the inner portion of the main body 32 of the electric toothbrush 31.

For example, a multi-axis (here the 3 axes of x, y, and z) acceleration sensor is used in the acceleration sensor 319. The output of each axes of the acceleration sensor 319 is input into the CPU 314 and is used to detect the 3 dimensional attitude of the brush unit 33.

A piezoresistive type, a capacitance type, or a micro electro mechanical systems (MEMS) heat sensing type can be preferably used for the acceleration sensor 319. Building the MEMS sensor on the inner portion of the main body 32 is simple since is extremely small-sized. However, the form of the acceleration sensor 319 is not limited to this and a sensor of an electrodynamic formula, a strain gage formula, a voltage formula, and the like may also be used.

Furthermore, while not specifically shown, it is good to provide a corrective circuit to correct the balance of the sensitivity of the sensor of each axis, the sensitivity of the temperature characteristics, the temperature drift, and the like. Furthermore, a band pass filter (low pass filter) for removing a dynamic acceleration component and noise may be provided. Furthermore, noise may be reduced by smoothing the output waveform of the acceleration sensor.

The system of the present embodiment mounts the main body 32 and is provided with the charging unit 3100 for charging the electric toothbrush 31 and the display unit 3110 for outputting the brushing effect. When charging the charging battery 313, it is possible to charge by non-contact electromagnetic induction just by mounting the main body 32 on the charging unit 3100.

The display unit 3110 is provided with a data receiving module 3111 that performs wireless communication with the data sending module 316 provided on the inside of the main body 32 of the electric toothbrush 31, and a display 3112 for outputting the data of the brushing result and the like received from the receiving module 3111.

Figure 15:
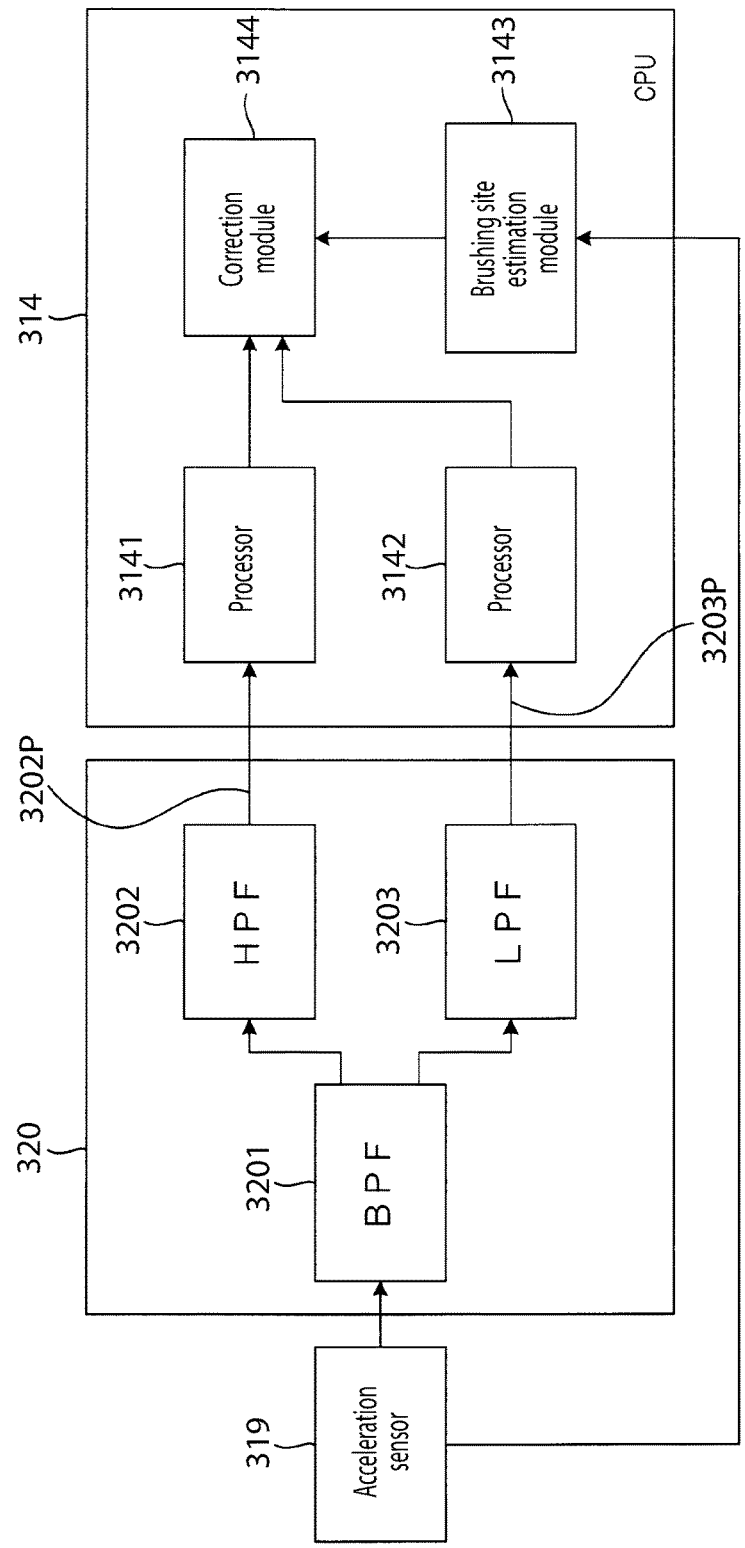
FIG. 15 is a schematic of an acceleration sensor and peripheral circuit according to an embodiment.

FIG. 15 is a diagram schematically illustrating the acceleration sensor 319 and a peripheral circuit thereof according to one embodiment. As illustrated in FIG. 15, the filter module 320 is connected to the acceleration sensor 319. The CPU 314 is connected to the filter module 320. Furthermore, the acceleration sensor 319 is connected directly to the CPU 314.

The filter module 320 receives the output signal from the acceleration sensor 319 and has a Band Pass Filter (BPF)

3201 that passes through only the signal of the specified frequency zone a High Pass Filter (HPF) 3202 connected in parallel to the BPF 3201, and a low pass filter (LPF) 3203.

The HPF 3202 passes through only a first 3202P signal of a frequency of a specified cut off frequency (for example, several hundred to several thousand Hz) or more that is a first threshold out of an input signal from the BPF 3201, and outputs to a processor 3141. The first threshold is the first signal 3202P output from the HPF 3202 being set to a large value to an extent reflecting a moveable component of the electric toothbrush 31 occurring by the brush unit 3 being oscillated at high speed by the motor 311.

The LPF 3203 passes through only a second 3203P signal of a frequency of a specified cut off frequency (for example, several Hz) or less that is a second threshold out of an input signal from the BPF 3201, and outputs to a processor 3142. The second threshold is the second signal 3203P output from the LPF 3203 being set to a small value to an extent reflecting when the electric toothbrush 31 moves much more slowly than the oscillation of the brush unit 33 and a moveable component.

The HPF 3202 and the LPF 3203 function as a signal extraction module that extract the first signal 3202P and the second signal 3203P from the output signal of the acceleration sensor 319. The first signal 3202P is a high frequency signal to the second signal 3203P. In other embodiment, the signal extraction module can be any device for obtaining the first and second signals from the output of the acceleration sensor.

The CPU 314 is provided with the processor 3141, the processor 3142, a brushing site estimation module 3143, and a correction module 3144. Each of these modules is function block realized by carrying out the program that the CPU 314 housed in the memory 315.

The processor 3141 seeks the amplitude of each waveform of the high-frequency first signal 3202P output from the HPF 3202 and calculates the variation amount in the specified period on the sought amplitude.

The processor 3142 seeks the amplitude of each waveform of the low frequency second signal 3203P output from the LPF 3203.

The brushing site estimation module 3143 can use the algorithm described in Japanese Unexamined Patent Application Publication No. 2009-240760, or Japanese Unexamined Patent Application Publication No. 2011-156204, which are hereby incorporated by reference in their entireties. These algorithms are based on the output signal from the acceleration sensor 319 to estimate the site being contacted by the brush portion of the brush unit (the brushing site).

The correction module 3144 corrects the brushing site estimated by the brushing site estimation module 3143 based on the amplitude of the first signal 3202P sought by the processor 3141 and the amplitude of the second signal 3203P sought by the processor 3142.

Figure 16:
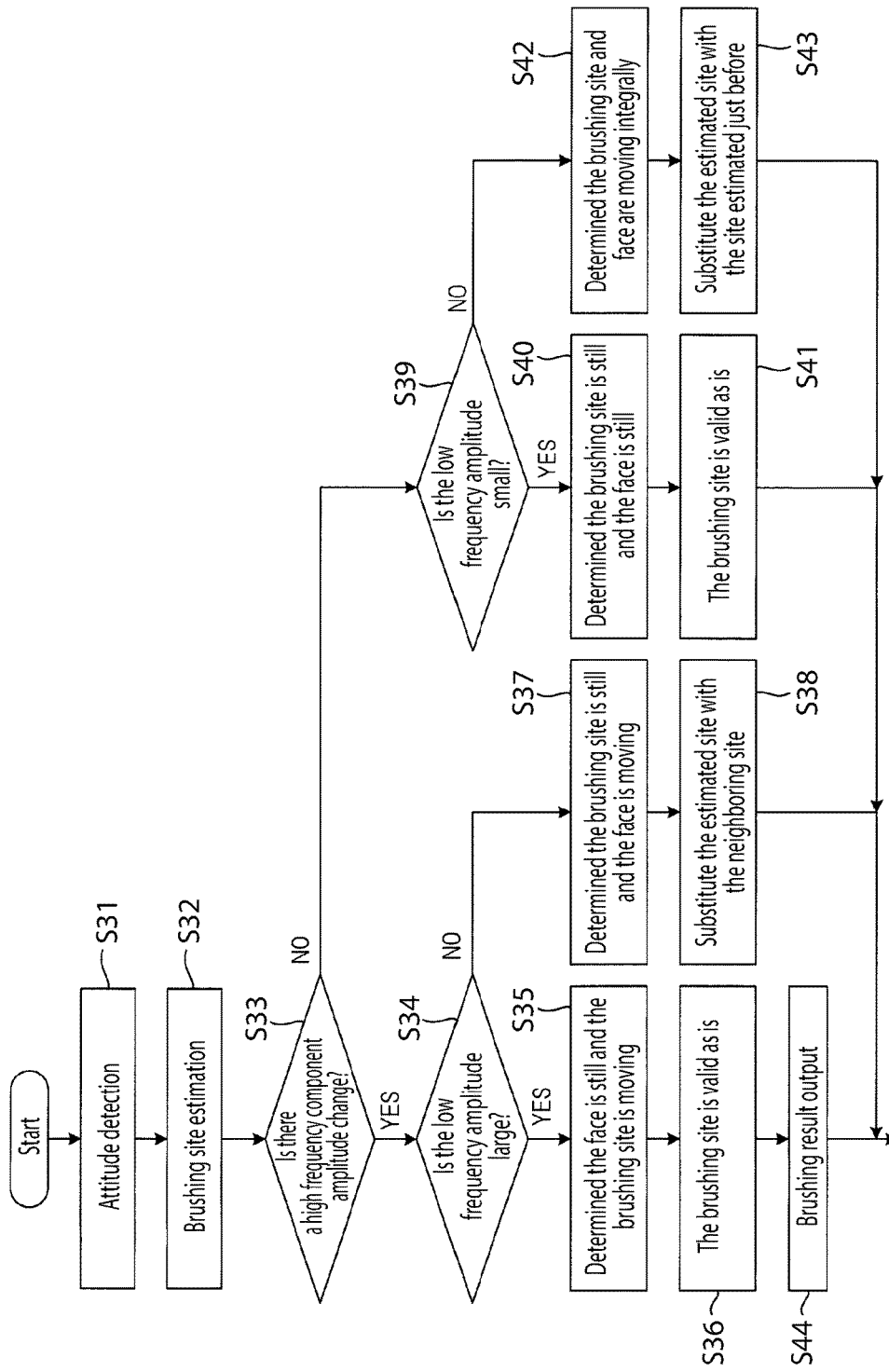
FIG. 16 is a flow chart for describing the brushing site estimation process according to an embodiment.

FIG. 16 is a flow chart for describing the estimation process of the brushing site in the electric toothbrush 31 according to an embodiment. When the switch 312 is operated and the power supply of the electric toothbrush 31 is ON, the CPU 314 performs a process that formats each portion, and the brushing site estimation module 3143 detects the attitude (slant) of the brush based on the output of the acceleration sensor 319 (step S31).

Next, the brushing site estimation module 3143 estimates the brushing site based on the attitude detected by the step S31 (step S32).

Next, the correction module 3144 determines, based on the output signal of the processor 3141, whether or not the amplitude of the first signal 3202P has changed, that is to say, whether or not the variation amount of the amplitude of the first signal 3202P is at the third threshold or above (step S33).

During teeth brushing, the brush unit 33 will move along with the row of teeth while contacting the row of teeth. In a state in which the brush portion of the brush unit 33 is contacting one tooth contained in the row of teeth, the amplitude of the first signal 3202P will change at a practically fixed value. That is to say, the variation amount of amplitude of the first signal 3202P is small in a fixed time.

When the brush unit 33 moves along the row of teeth, the brush portion passes through the interdental space. When the brush portion passes through the interdental space, the amplitude of the first signal 3202P gets smaller in this time because time occurs where the brush unit is not in contact with the tooth.

That is to say, from a state where the brush portion is in contact with an arbitrary tooth, when moving the brush portion from this tooth to a neighboring tooth, the amplitude of the first signal 3202P returns to a first value after the amplitude changes to a second value smaller than the first value from the state of the first value. In this manner, the variation amount of amplitude of the first signal 3202P gets larger in a fixed time.

Therefore, it can be distinguished by the size of the variation amount of amplitude of the first signal 3202P whether the brush unit 33 is still regarding the tooth or whether the brush unit 33 is moving regarding the tooth. Because of this distinguishing, the step S33 processing is performed.

If the determination of the step S33 is YES, it can be determined that the brush unit 33 is moving with respect to the tooth, and if the determination of the step S33 is NO, it can be determined that the brush unit 33 is still with respect to the tooth.

When the determination of the step S33 is YES, the correction module 3144 determines whether or not the amplitude of the second signal 3203P is large, that is to say, whether or not the amplitude of the second signal 3203P exceeds a fourth threshold based on the output signal of the processor 3142 (step S34).

The pattern in which the brush unit 33 moves with respect to the tooth has a first pattern in which only the electric toothbrush moves in a state where the face is still and a second pattern in which the only the face moves in a state where the electric toothbrush 31 is still.

The amplitude of the second signal 3203P in the first pattern becomes larger because the electric toothbrush is moving. On the other hand, the amplitude of the second signal 3203P in the second pattern becomes a sufficiently smaller value than the first pattern (a value of the fourth threshold or less) because the electric toothbrush 31 is still.

Therefore, it can be distinguished whether it is the first pattern or the second pattern by the determination in step S34.

When the determination of the step S34 is YES (the amplitude of the second signal 3203P exceeds the fourth threshold), the correction module 3144 distinguishes that "the face is still and the brush portion is moving" (step S35).

When it is distinguished that "the face is still and the brush portion is moving," the reliability of the brushing site estimated based on the output signal of the acceleration sensor 319 is high. Because of this, the correction module 3144 makes the brushing site estimated by the brushing site estimation module 3143 effective as it is after the step S35 (step S36).

When the determination of the step S34 is NO (the amplitude of the signal 3203P is the fourth threshold or less), the correction module 3144 distinguishes that "the face is moving and the brush portion is still" (step S37).

When it is distinguished that "the face is moving and the brush portion is still," the reliability of the brushing portion estimated based on the output signal of the acceleration sensor 319 gets low. Because of this, the correction module 3144 corrects (substitutes) the brushing site estimated by the brushing site estimation module 3143 to the site neighboring that site (a site estimated to not yet be brushed) after the step S37 (step S38).

When the determination of step S33 is NO, the correction module 3144 determines whether or not the amplitude of the second signal 3203P is small, that is to say, whether or not the amplitude of the second signal 3203P is the fourth threshold or less based on the output of the processor 3142 (step S39).

When the correction module 3144 determines that the amplitude of the second signal 3203P to be small (step S39: YES), it distinguishes that "the face is still and the brush portion is also still" (step S40). In this case, the reliability of the brushing site estimated based on the output of the acceleration sensor 319 is high. Because of this, the correction module 3144 makes the brushing site estimated by the brushing site estimation module 3143 effective as it is (step S41).

When the correction module 3144 determines that the amplitude of the second signal 3203P is not small (step S39: NO), it distinguishes that "the face and the brush are moving integrally" (step S42). In this case, the reliability of the brushing site estimated based on the output of the acceleration sensor 319 is low. Because of this, the correction module 3144 corrects (substitutes) the brushing site estimated by the brushing site estimation module 3143 to the site estimated just before (step S43). That is to say, the correction module 3144 does not perform a renewal of the brushing site, but performs a process maintaining the brushing site estimated just before.

The CPU 314 is estimated as above, and outputs the corrected brushing site to the display unit 3110 (the display 3112) via the data sending module 316 (step S44).

As above, it is possible to improve the brushing site estimation accuracy based on the amplitude of a high frequency component and the amplitude of a low frequency component output from the acceleration sensor 319 provided on the electric toothbrush 31. Therefore, it becomes possible to perform effective brushing support.

Each process performed by the CPU 314 in the present embodiment can also be presented as a program for carrying out on a computer. Furthermore, the process performed by the filter 320 can also be presented as a program for carrying out on a computer. This manner of program is recorded to a non-temporary (non-transitory) recording medium as a program that can be read by the computer.

This manner of "recording medium that can be read by a computer" is, for example, an optical medium such as a Compact Disc-ROM (CD-ROM), and includes magnetic recording mediums such as a memory card. Furthermore, this manner of program can also be presented by download via a network.

It should be thought that all of the points of the embodiment shown this time are examples and are not limited. The scope of the present invention is not the above description, but is illustrated in the scope of claims, and all of the changes having meaning equal to the scope of claims and within the scope are implied to be included.

As described above, the below matters are shown in the present specification. The electric toothbrush shown is comprised of a driving module that oscillates the brush unit, an acceleration sensor, a signal extraction module that extracts the first signal derived from the frequency being at the first threshold or more and the second signal derived from the frequency being at the second threshold or below from the output signal of the acceleration sensor, a brushing site estimation module that estimates the brushing site by the brush unit based on the output signal of the acceleration sensor, and a correction module that corrects the brushing site estimated by the brushing site estimation module based on the amplitude of the first signal and the amplitude of the second signal.

The electric toothbrush shown is something wherein the correction module performs corrections in the first case wherein the variation amount of the amplitude of the first signal is at the third threshold or more and when variation amount of the amplitude of the second signal is at the fourth threshold or less, or in the second case wherein the variation amount of the amplitude of the first signal is less than the third threshold and the amplitude of the second signal exceeds the fourth threshold.

The electric toothbrush shown is something wherein the correction module substitutes the brushing site estimated by the brushing site estimation module to the neighboring site in the first case.

The electric toothbrush shown is something wherein the correction module substitutes the brushing site estimated by the brushing site estimation module to the brushing site estimated by the brushing site estimation module in a state just before the variation amount of the amplitude of the first signal becomes less than the third threshold.

The brushing site estimation method shown is a brushing site estimation method by an electric toothbrush having a driving module that oscillates the brush unit and an acceleration sensor, and is provided with a signal extraction step that extracts the first signal achieved from the frequency of the first threshold or more and the second signal achieved from the frequency of the second threshold or less, a brushing site estimation step that estimates the brushing site by the brush unit based on the output signals of the acceleration sensor, and a correction step that corrects the brushing site estimated by the brushing site estimation step.

The present invention has especially high convenience applied as a household use electric toothbrush and is effective.

While the inventions have been described with respect to specific examples, those skilled in the art will appreciate that there are numerous variations and permutations of the above described inventions. It is to be understood that other embodiments may be utilized and structural and functional modifications may be made without departing from the scope of the present inventions. Thus, the spirit and scope should be construed broadly as set forth in the appended claims.

What is claimed is:

1. An electric toothbrush comprising:
a trajectory detecting module configured to detect a trajectory of movement of a brush, the trajectory comprising a plurality of positions;
an attitude detecting module configured to detect an attitude of the brush;

a site estimating module configured to estimate a brushing site for each of the plurality of positions of the trajectory, each estimated brushing site being based on the trajectory detected by the trajectory detecting module; and a back most tooth detecting module configured to detect a back most tooth based on a change of the attitude detected by the attitude detecting module;

wherein the site estimating module is further configured to correct the estimated brushing site for each of the plurality of positions of the trajectory based on the estimated site of the detected back most tooth.

2. The electronic toothbrush device according to claim 1 wherein the back most tooth detecting module detects the back most tooth based on the change of the attitude being greater than a predetermined amount.

3. The electronic toothbrush device according to claim 1 wherein the back most tooth detecting module detects a returning point at a back most side of movement of the brush as the back most tooth.

4. The electronic toothbrush device according to claim 1 wherein the site estimating module is further configured to estimate the brushing site for each of the plurality of positions of the trajectory based on the attitude detected by the attitude detecting module.

5. The electronic toothbrush device according to claim 1 further comprising an evaluation output module configured to evaluate and output brushing results for each brushing site.

6. The electronic toothbrush device according to claim 5 wherein the brushing results include brushing time, brush angle, and brush pressure.

7. The electronic toothbrush device according to claim 1 wherein the estimated brushing site for each of the plurality of positions of the trajectory is one of a maxillary front buccal surface, a maxillary front lingual surface, a maxillary left buccal surface, a maxillary left lingual surface, a maxillary left occlusal surface, a maxillary right buccal surface, a maxillary right lingual surface, a maxillary right occlusal surface, a mandibular front buccal surface, a mandibular front lingual surface, a mandibular left buccal surface, a mandibular left lingual surface, a mandibular left occlusal surface, a mandibular right buccal surface, a mandibular right lingual surface, and a mandibular occlusal surface.

8. The electronic toothbrush device according to claim 1 wherein the trajectory detecting module comprises at least one of an acceleration sensor, an angular velocity sensor, and a geomagnetic sensor.

9. The electronic toothbrush device according to claim 1 wherein the attitude detecting module comprises at least one of an acceleration sensor, an angular velocity sensor, and a geomagnetic sensor.

10. The electronic toothbrush device according to claim 1 further comprising a camera configured to obtain an image in the mouth, the estimated brushing site further based on the obtained image.

11. A method of estimating brushing sites, the method comprising:
    detecting a trajectory of movement of a brush, the trajectory comprising a plurality of positions;
    detecting an attitude of the brush;
    estimating a brushing site for each of the plurality of positions of the trajectory, each estimated brushing site being based on the trajectory detected;
    detecting a back most tooth based on a change of the attitude detected by the attitude detecting module; and
    correcting the estimated brushing site for each of the plurality of positions of the trajectory based on an estimated site of the detected back most tooth.

12. The method according to claim 11 wherein the detection of the back most tooth is based on the change of the attitude being greater than a predetermined amount.

13. The method according to claim 11 wherein the detection of the back most tooth includes detecting a returning point at a back most side of movement of the brush as the back most tooth.

14. The method according to claim 11 wherein the estimation of the brushing site for each of the plurality of positions of the trajectory is further based on the attitude detected.

15. The method according to claim 11 further comprising evaluating and outputting brushing results for each brushing site, wherein the brushing results include brushing time, brush angle, and brush pressure.

16. The method according to claim 11 wherein the estimated brushing site for each of the plurality of positions of the trajectory is one of a maxillary front buccal surface, a maxillary front lingual surface, a maxillary left buccal surface, a maxillary left lingual surface, a maxillary left occlusal surface, a maxillary right buccal surface, a maxillary right lingual surface, a maxillary right occlusal surface, a mandibular front buccal surface, a mandibular front lingual surface, a mandibular left buccal surface, a mandibular left lingual surface, a mandibular left occlusal surface, a mandibular right buccal surface, a mandibular right lingual surface, and a mandibular occlusal surface.

17. The method according to claim 11 wherein the detection of the trajectory of movement of the brush is carried out by at least one of an acceleration sensor, an angular velocity sensor, and a geomagnetic sensor.

18. The method according to claim 11 wherein the attitude of the brush is detected by at least one of an acceleration sensor, an angular velocity sensor, and a geomagnetic sensor.

19. The method according to claim 11 further comprising obtaining an image in the mouth, the estimated brushing site further based on the obtained image.

20. A non-transitory computer-readable storage medium encoded with instructions which, when executed on a processor, perform a method of:
    detecting a trajectory of movement of a brush, the trajectory comprising a plurality of positions;
    detecting an attitude of the brush;
    estimating a brushing site for each of the plurality of positions of the trajectory, each estimated brushing site being based on the trajectory detected;
    detecting a back most tooth based on a change of the attitude detected by the attitude detecting module; and
    correcting the estimated brushing site for each of the plurality of positions of the trajectory based on an estimated site of the detected back most tooth.

* * * * *